United States Patent

Schick et al.

[11] Patent Number: 5,908,294
[45] Date of Patent: Jun. 1, 1999

[54] DENTAL IMAGING SYSTEM WITH LAMPS AND METHOD

[75] Inventors: David B. Schick, Flushing; Jonathan Singer, Dobbs Ferry; Valery Bratslavsky, Brooklyn; Anthony A. Scott, Bronx, all of N.Y.

[73] Assignee: Schick Technologies, Inc, Long Island City, N.Y.

[21] Appl. No.: 08/873,806

[22] Filed: Jun. 12, 1997

[51] Int. Cl.$^6$ ..................................................... A61C 1/00
[52] U.S. Cl. ............................. 433/29; 600/160; 600/179
[58] Field of Search ............................. 433/29; 600/101, 600/109, 129, 160, 175, 179

[56] References Cited

U.S. PATENT DOCUMENTS

| | | | |
|---|---|---|---|
| 1,704,397 | 3/1929 | Meitzler | 600/249 |
| 2,038,911 | 4/1936 | Stutz et al. | 240/2 |
| 2,788,390 | 4/1957 | Sheldon | 178/6.8 |
| 4,230,453 | 10/1980 | Reimers | 433/29 |
| 4,575,805 | 3/1986 | Moermann et al. | 364/474 |
| 4,858,001 | 8/1989 | Milbank et al. | 358/98 |
| 4,994,910 | 2/1991 | Williams | 358/98 |
| 5,124,797 | 6/1992 | Williams et al. | 358/225 |
| 5,267,857 | 12/1993 | Sickler | 433/29 |
| 5,363,135 | 11/1994 | Inglese | 348/70 |
| 5,429,502 | 7/1995 | Cooper et al. | 433/29 |
| 5,487,661 | 1/1996 | Peithman | 433/29 |
| 5,512,036 | 4/1996 | Tamburrino et al. | 600/172 |
| 5,523,782 | 6/1996 | Williams | 348/66 |
| 5,527,261 | 6/1996 | Monroe et al. | 600/109 |
| 5,634,790 | 6/1997 | Pathmanabhan et al. | 433/29 |
| 5,702,249 | 12/1997 | Cooper | 433/29 |
| 5,722,403 | 3/1998 | McGee et al. | 600/373 |
| 5,751,341 | 5/1998 | Chaleki et al. | 600/117 |

*Primary Examiner*—John J. Wilson
*Attorney, Agent, or Firm*—Fitzpatrick, Cella, Harper & Scinto

[57] ABSTRACT

A handheld dental video camera and a corresponding method is disclosed. The dental video camera includes a window for receiving light. In some aspects of the invention, a lamp is mounted distally beyond the window and aimed to illuminate a subject. In other aspects of the invention, a white LED is used to illuminate the subject.

18 Claims, 7 Drawing Sheets

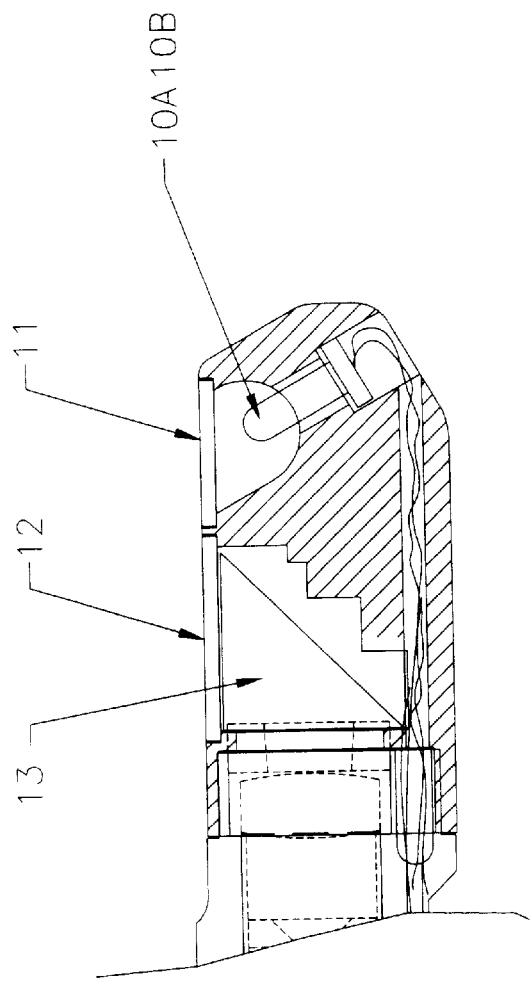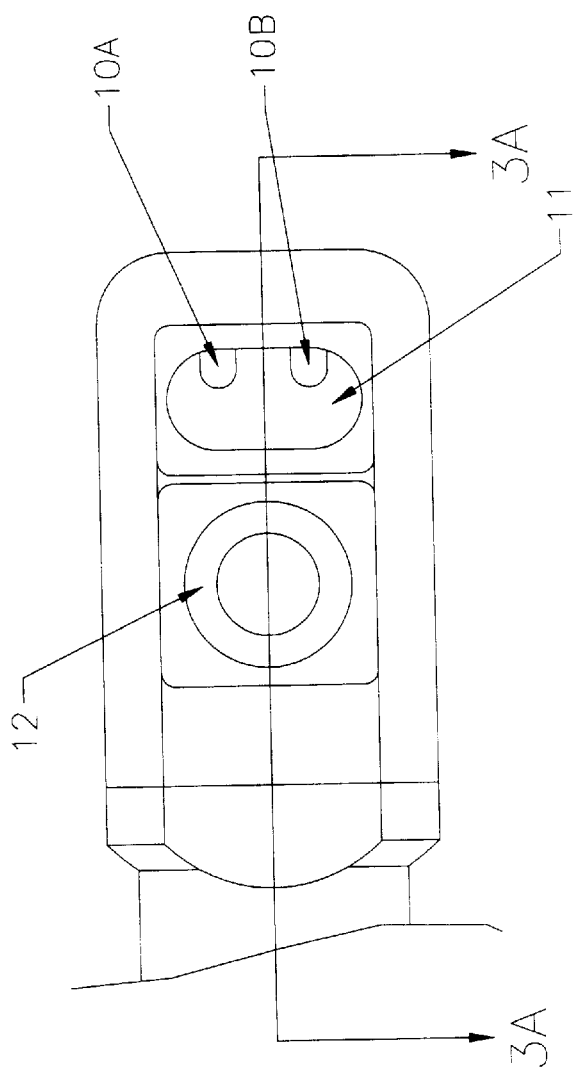
FIG 3A
FIG 3B

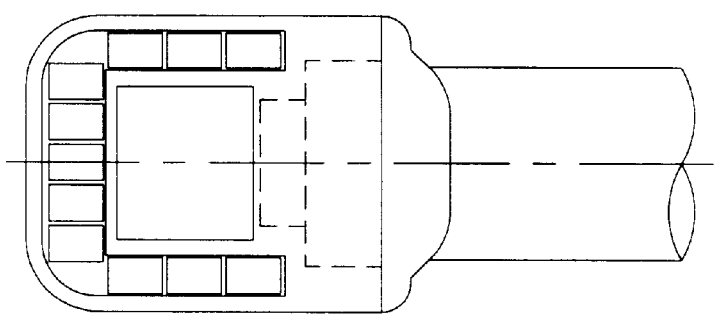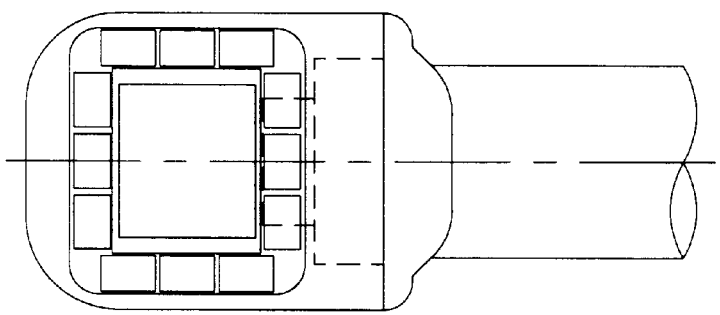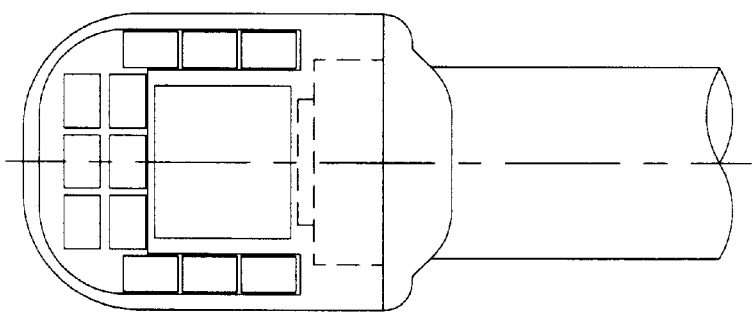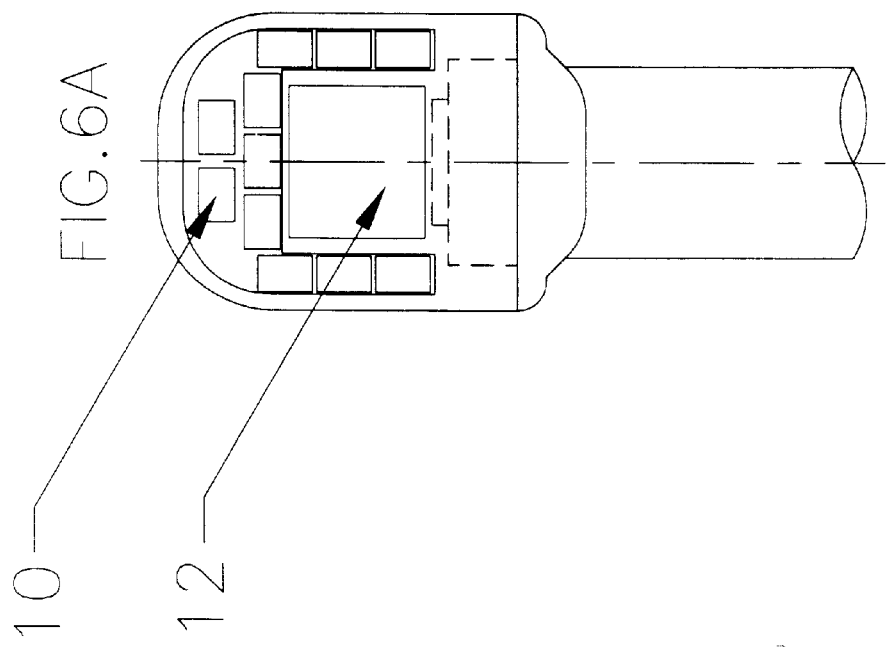

DENTAL IMAGING SYSTEM WITH LAMPS AND METHOD

BACKGROUND OF THE INVENTION

This invention relates to the field of video imaging and, more specifically, to a video imaging apparatus for use in dental imaging.

Video imaging cameras have been used for obtaining images in dentistry for some time. One example of an existing system can be found in U.S. Pat. No. 5,523,782 (Williams), which describes a video dental camera that includes a light source, a CCD, and an adjustable focus lens system. Other examples of existing system can be found in U.S. Pat. No. 4,575,805 (Moermann et al.), and in U.S. Pat. No. 5,527,261 (Monroe et al.).

Until now, however, it has been extremely difficult to fashion a sufficiently slim instrument. Slim instruments are desirable because they provide accessibility to places that thicker instruments can not reach. Moreover, even in cases where a thick instrument can provide adequate access, the slimmer instruments can reduce the discomfort experienced by the patient.

One factor contributing to the thickness of previous dental video cameras is the type of light source that is incorporated into the camera head. Some previous dental cameras, such as the one described in U.S. Pat. No. 5,429,502, use an external light source and route the light from the source to the head using fiber optics. This arrangement, however, requires the optical fibers to travel through the cable and through the body of the handheld camera unit, which results in a stiffer cable (which can reduce maneuverability) and a thicker handheld unit. In addition, the fiber optic connections require a more complex and expensive connector, as compared to fully electrical connectors. Finally, using fiber optics to illuminate the subject requires increased power, because some of the light energy is lost in the optical fiber.

Other prior art imaging devices use lamps at the end of the imaging head instead of fiber optics. But until now, lamps have not been used in configurations that minimize the thickness of the instrument. For example, the lamps in Williams are positioned axially away from the imaging window, and the lamp in Moermann is positioned on the proximal side of the imaging window. Both of these configurations result in relatively thick instruments.

In addition, the lamps used in previous imaging devices had significant shortcomings. One example is the halogen lamp used in Monroe, which consumes significant power and generates heat. Another example is the LED used in Moermann, which, like all ordinary LEDs, produces essentially monochromatic light that can make diagnosis of certain medical conditions difficult.

SUMMARY OF THE INVENTION

The present invention advantageously avoids the aforementioned drawbacks by providing a novel lamp arrangement that results in a slimmer instrument.

The present invention also advantageously avoids the aforementioned drawbacks by using white LEDs or sequentially energized colored lights in place of the lamps used in prior dental video cameras.

According to one aspect of the invention, a dental video camera is provided. This video camera includes a housing and a window, located near the distal end of the housing, for receiving light reflected from a subject. The camera includes light directing means for directing the received light in a proximal direction and an image sensor mounted on the proximal side of the light directing means so that the light directed by the light directing means strikes the image sensor. The camera also includes a lamp mounted distally beyond the window, aimed to illuminate the subject.

According to another aspect of the invention, a dental video camera is provided. This video camera includes a housing with a window for receiving light reflected from a subject, an image sensor, light directing means for directing the received light towards the image sensor, and a white LED and aimed to illuminate the subject.

According to another aspect of the invention, a dental video camera is provided. This video camera includes a housing and a window, located near the distal end of the housing, for receiving light reflected from a subject. The camera also includes a lens for directing the received light in a proximal direction, an image sensor mounted on the proximal side of the lens for receiving the light directed by the lens, and a white LED aimed to illuminate the subject.

According to another aspect of the invention, a method of using an image sensor to obtain an image of a dental subject is provided. This method includes the steps of illuminating the dental subject with light from a white LED, receiving light reflected from the subject, and directing the received light towards the image sensor.

According to another aspect of the invention, a dental video camera is provided. This video camera includes an image sensor, three light sources for producing three colors of light, and a controller for controlling the illumination of the light sources according to a pattern. An image sensor receives the light from the light sources that has been reflected by a subject, and generates output signals in accordance with the received light. An image processor then generates a video signal based on the outputs of the image sensor.

BRIEF DESCRIPTION OF THE DRAWINGS

FIG. 3A is a cross-sectional view of a distal fragmented portion of the camera taken from section line 3A—3A in FIG. 3B.

FIG. 3B is a bottom view of the distal fragmented portion of the camera.

FIGS. 6A–6D show alternate arrangements of lamps about the imaging window.

DETAILED DESCRIPTION OF THE PREFERRED EMBODIMENTS

Figure 1:
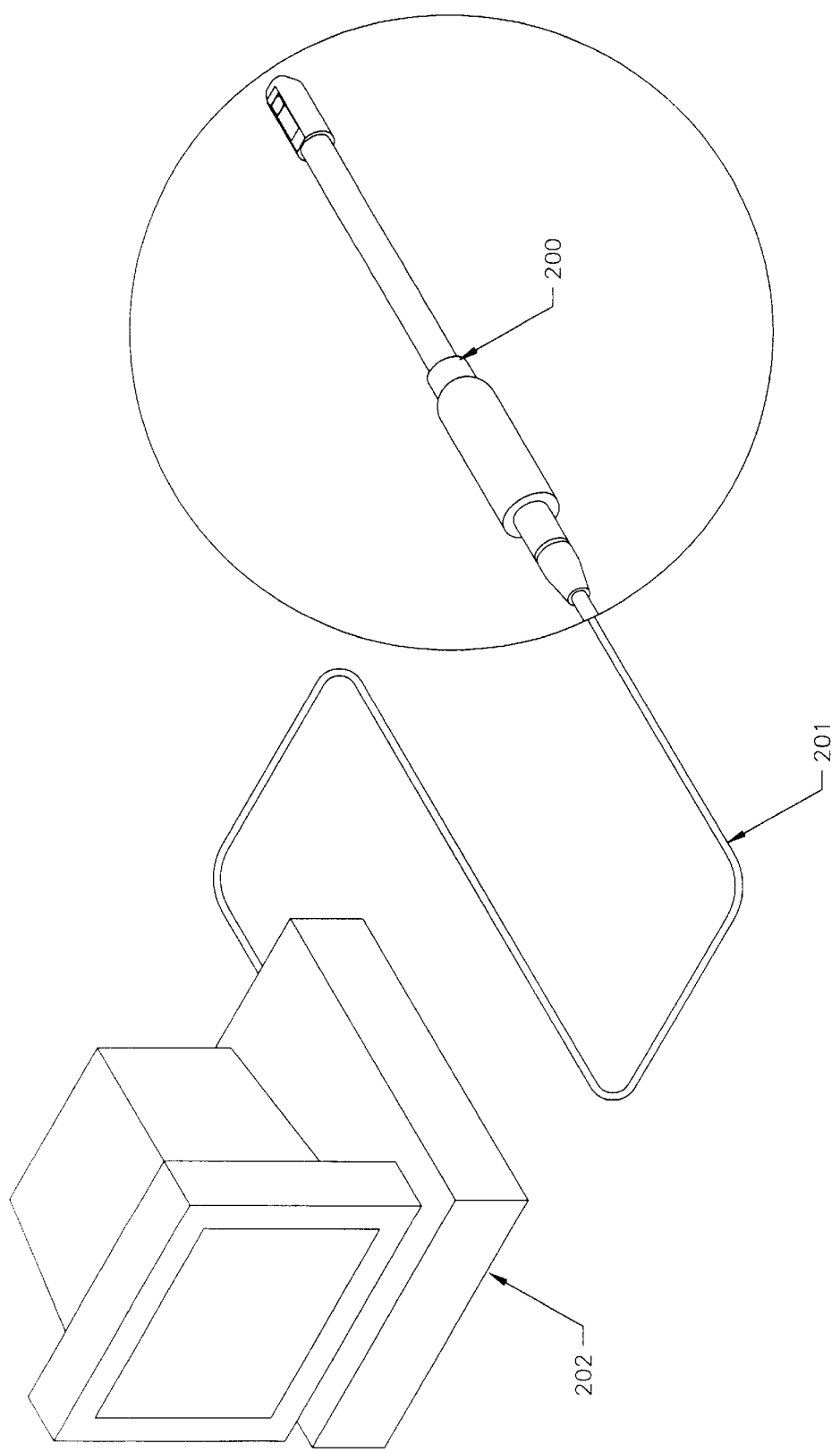
FIG. 1 depicts an embodiment of an electronic video dental camera and image processing system in accordance with the present invention.

FIG. 1 shows a dental video camera system including a handpiece 200 and an image processing system 202. The handpiece 200 is connected to the image processing system 202 via a connecting cord 201.

Figure 2:
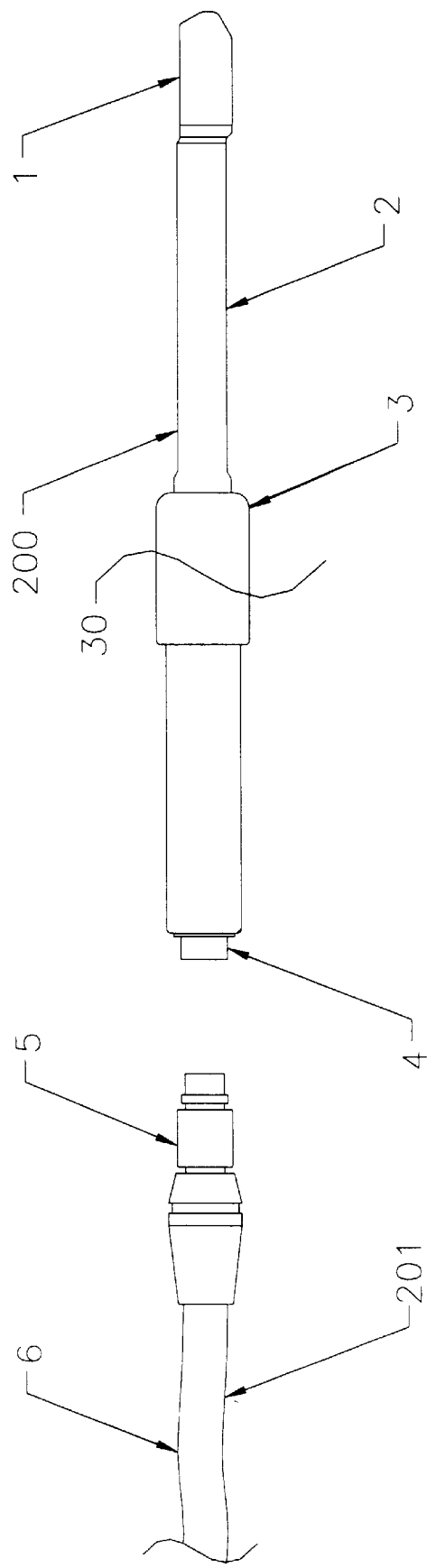
FIG. 2 is an external side view of the camera showing the handpiece and the end of the connecting cord.

FIG. 2 shows the handpiece 200 which has a distal end 1, a median section 2, a focusing ring 3, and a mini circular connector 4 at the proximal end of the handpiece. The connector 4 mates with a matching mini circular connector 5, which terminates the video cable 6. Signals originating from an image sensor (not shown) housed inside the handpiece 200 travel through the connector 4, the connector 5, and the video cable 6 on their way to the image processing system 202 (shown in FIG. 1).

FIGS. 3A and 3B show details of the distal end 1 of one embodiment of the handpiece, which includes an imaging window 12 and light sources 10a and 10b. The imaging window receives light reflected by the subject. The light sources 10a and 10b, which are located distal to the imaging window 12 and are covered by a protective glass shield 11, are aimed so that they will provide illumination for subjects located below the window. A prism 13 is located within the distal end of the handpiece 1, angled in relation to the imaging window 12 to direct the light arriving through the imaging window in the direction of the proximal end of the handpiece. Of course, instead of using an individual imaging window 12 and shield 11, as depicted in the figure, a single piece of material may be used as both the window and the shield. In this configuration, the material would have a window portion and a shield portion distal to the window portion.

A wide variety of lamps may be used. A low-power, long life lamp is preferable to save power and minimize service calls and system down time. One example of a suitable lamp is an incandescent light bulb, such as Gilway Technical Lamp # 4115. Another example is a "white LED". This white LED could comprise, for example, a short-wavelength LED combined together with a phosphorescent coating, such as Nichia America # NSCW-100.

The "white LED" could also comprise, for example, a set of three single color LEDs (e.g., red, green, and blue), mounted in a single package, such as Nichia America # NSCM-310. While two lamps are depicted in the figure, any number of lamps may be used. In addition to generating light, the lamps also generate some heat. This is advantageous in dental applications, because it helps clear away condensation that could form from a patient's breathing on a cold instrument.

By locating the lamps in the distal end of the handpiece, distal to the imaging window, and angling the lamps so as to provide direct illumination of the object being imaged, the diameter of the housing can be minimized. This allows the present invention to be contained within a slimmer housing, as compared to prior art cameras which have light sources positioned above the imaging window, such as the one described in U.S. Pat. No. 4,575,805 (Moermann et al.). A slimmer device is advantageous for dental use.

Alternative light source arrangements may also be used. For example, FIGS. 6A, 6B, and 6D show a number of light sources 10 arranged on three sides of the imaging window 12. FIG. 6C shows a number of light sources arranged on four sides of the imaging window. Numerous other light source arrangements can be readily envisioned.

Aiming of the light sources depends on both the arrangement of the light sources around the window and the type of light source used. For example, when incandescent lamps are used in the configuration shown in FIG. 3B, the lamps should be angled as shown in the figure so that the light is directed back towards the proximal end. When LEDs are used in any of the configurations depicted in FIGS. 6A–6D, the LEDs can be aimed perpendicular to the surface of the instrument, because the light is sufficiently diffused to illuminate the subject.

Figure 4:
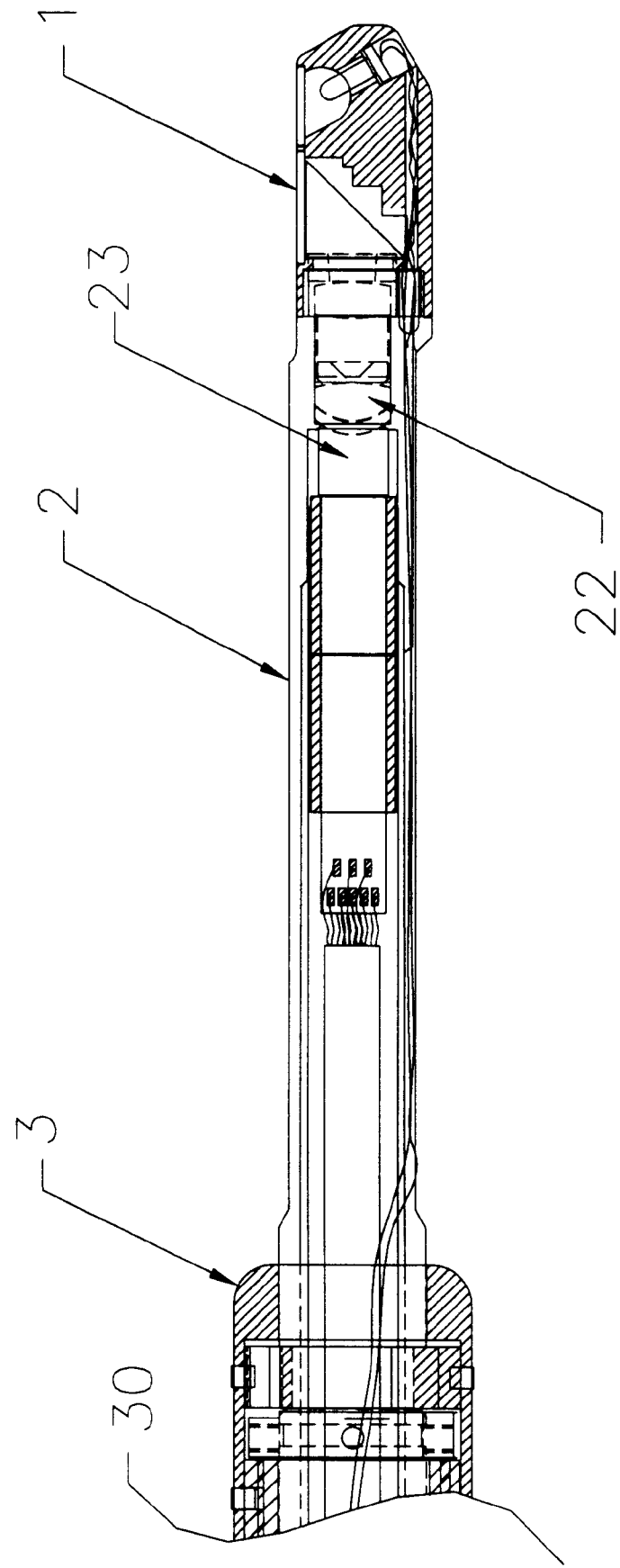
FIG. 4 is a cross-sectional view of the camera, showing detail in the median portion.

FIG. 4 shows details of the median section 2 of the handpiece, which houses the lens system 22, the image sensor 23, and the focusing mechanism 3. The lens system 22 is preferably a fixed-focus lens system. The image sensor 23 is preferably either a CCD (charge coupled device) or an APS (active pixel sensor array).

The lens system 22 is located in the distal portion of the median section 2, proximal to the distal end of the handpiece 1. The movable image sensor 23 is located proximal to the fixed lens system 22. The lens system 22 transmits the light arriving from the distal end of the handpiece 1 to the active surface of the image sensor 23. The lens system 22 may be replaced by another type of light direction means including, for example, a mirror, a prism, and an optical fiber.

The movable image sensor 23 is controlled by a plunger system which is attached to the focusing ring 3. Preferably, the focusing ring 3 can be manually rotated into any of a plurality of detented positions that correspond to a plurality of image sensor positions.

One preferred embodiment uses four detented positions. When the focusing ring 3 is rotated into each of the four various positions, the image sensor, which is mechanically coupled to the plunger system, is moved nearer to or farther from the fixed lens system 22 along a proximal-to-distal axis, depending on the degree of rotation. Each of these positions has an associated focal setting and depth of field. Most preferably, the approximate focal range settings are: (1) 1 to 6 mm; (2) 5–15 mm; (3) 12–25 mm; and (4) 180 mm–∞. This selection of focal range settings is optimized for dental imaging by minimizing the required amount of manipulation while maximizing image quality and ease of use. For a system using a 3.65 mm×2.74 mm rectangular CCD image sensor and a lens with a focal length of 4.50 mm, the total range of movement of the image sensor needed to obtain these focal settings is approximately 2 mm. If the amount of light supplied to the subject is increased, the depth of field can be extended by reducing the aperture of the lens. This would allow a reduction in the number of focus ranges.

Figure 5:
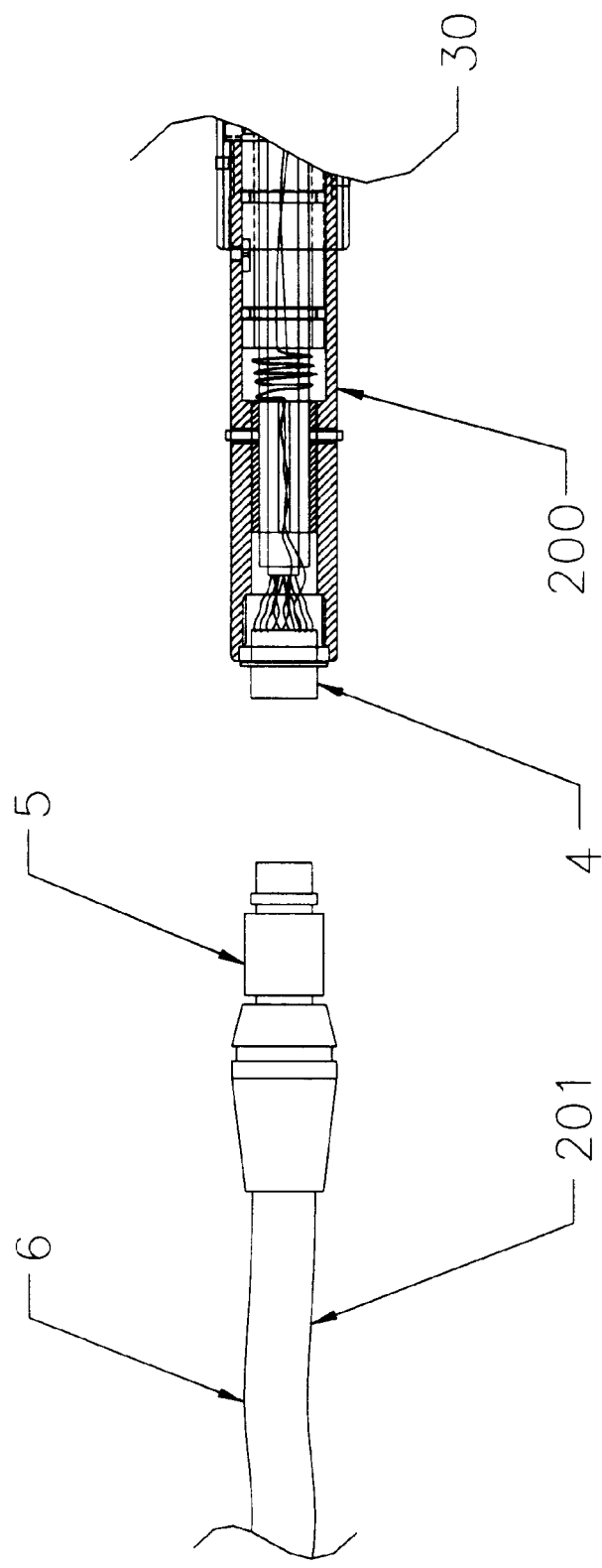
FIG. 5 is a view of the proximal portion of the handpiece and the distal portion of the connecting cord assembly.

FIG. 5 shows a sectional view of the proximal end of the handpiece 200, as well as the distal end of the connecting cord assembly 201. The mini circular connector 4 at the proximal end of the handpiece 200 mates with the connector 5 on the connecting cord assembly 201. Preferably, the connectors can be mated and released quickly. A suitable connector pair for this purpose includes, for example, parts Nos. HR25-9P-16 and HR25-9R16 made by Hirose Electric. The connecting cord assembly 201 includes a video cable 6 which is preferably flexible and lightweight. When the connector 4 is mated with the connector 5, the connecting cord assembly transmits the video image acquired by the image sensor in the handpiece to the image processing system (shown in FIG. 1). Some preprocessing (including, e.g., preamplification) may be performed by known means in the handpiece 200 before the image signals are sent to the image processing system.

Returning to FIG. 1, the image processing system 202 may be implemented in hardware, software or a combination of both. Two image processing settings may be selected: intraoral and extraoral. These settings correct for the quality and amount of light available and allow for realistic images to be acquired in both intraoral and extraoral locations, because ambient light is qualitatively different from lamp light. This feature is implemented by storing two different white balances in the image processing system (one for the extraoral setting and one for the intraoral setting) and processing the image using the appropriate stored white balance. The white balance processing adjusts the levels of the red, green, and blue components of the image to create an image in which white objects are perceived as being white.

A preferred approach of implementing the white balance processing uses the Panasonic GP-KS 162 CB camera control unit (CCU) together with a Panasonic GP-KS 462HM CCD. The CCU includes circuitry to interface with the CCD, white balance processing, and circuitry to generate an NTSC video signal. The CCU can store two white balances corresponding to two different types of light. For example, the white balance settings for the ambient light coming from a dentist's overhead light and from the camera's light source can be stored. When the dentist uses the camera, the appropriate white balance setting can be selected instantaneously without recalibrating the white balance for each exposure.

The preferred CCU can compensate for white balances ranging from 2,200–10,000° K. of color temperature. Incandescent lamps and both types and white LEDs are available within that temperature range. For those parts that have a wide range of color temperature, samples with the appropriate color temperature should be selected.

In the case of intraoral imaging, very little ambient light is available. When the camera is switched to the intraoral setting, the light source located in the head of the camera can be automatically switched on. In this mode, the image is processed using a stored white balance corresponding to the quality of the lamps which provide illumination (e.g., the incandescent bulbs or LEDs described above). In the case of extraoral imaging, ambient light is available. When the camera is switched to the extraoral setting, the light source can be automatically turned off. Due to the presence of ambient light, a different stored white balance is used to process the image.

The embodiments described above involve illuminating the subject with white light and detecting the light using a sensor that is sensitive to white light. An alternative embodiment uses a monochromatic sensor and strobes of different colored monochromatic light to attain the same effect as white illumination.

Figure 7:
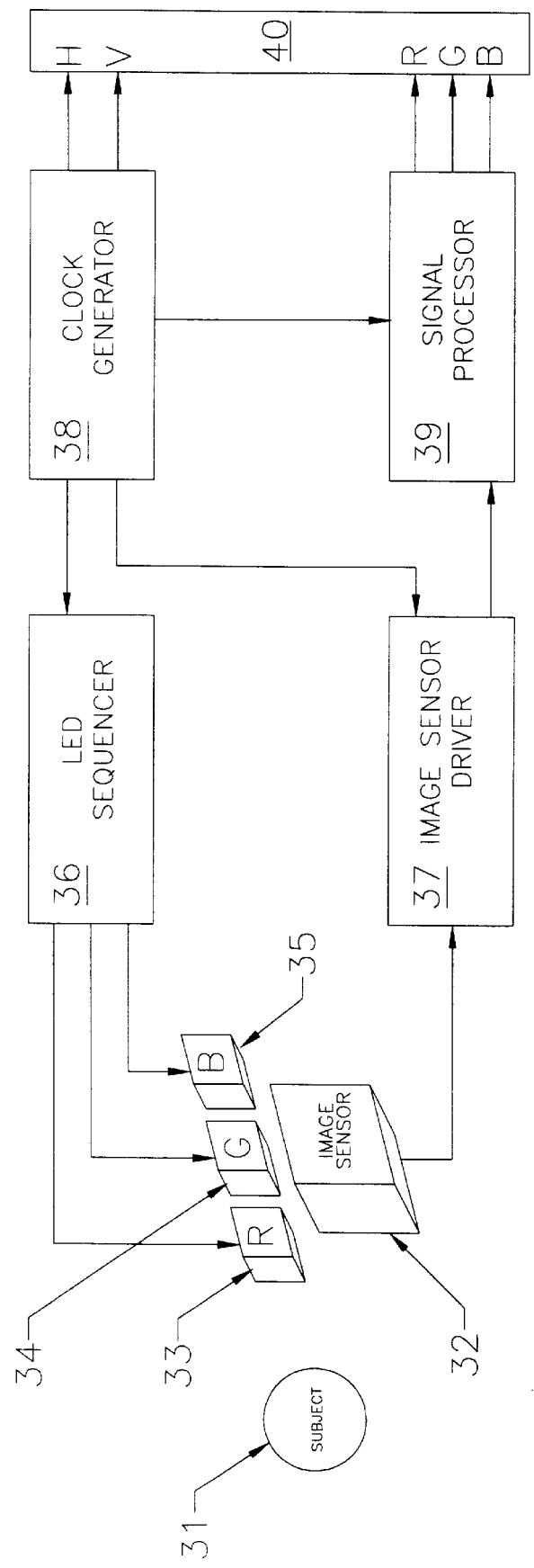
FIG. 7 is a block diagram of a strobed illumination system for the camera.

FIG. 7 depicts an embodiment that uses this strobed configuration. In this embodiment, instead of illuminating the subject with white light, the subject is strobed with each of the components of white light (red, green, and blue) sequentially. During each strobe period, the output from the image sensor is captured. The image sensor outputs from the three strobe periods are then combined by a signal processor to form a standard RGB video signal.

The clock generator 38 provides timing signals to synchronize the circuit. The LED sequencer 36 receives a clock signal from the clock generator 38, and turns on each of the LEDs 33–35 in turn, in three phrases. During the first phase, the LED sequencer 36 turns on the red LED 33. During the second phase, the LED sequencer 36 turns on the green LED 34. During the third phase, the LED sequencer 36 turns on the blue LED 35. This sequence of phases repeats continuously.

The clock generator 38 also sends signals to the image sensor driver 37. The image sensor 32 receives light that originated from one of the LEDs 33–35, bounced off a subject 31, and onto the image sensor 32. The output of the image sensor is received by the image sensor driver 37. When the red LED 33 is illuminated, the image sensor will capture an image of the subject 31 illuminated by red light.

When the green LED 34 is illuminated, the image sensor will capture an image of the subject illuminated by green light. Similarly, when the blue LED 34 is illuminated, the image sensor will capture an image of the subject illuminated by blue light.

The signal processor 39 receives these three images from the image sensor driver 37, together with synchronizing signals from the clock generator 38. The signal processor combines three image signals into ordinary RGB signals which are provided to a video signal interface 40. The clock generator 38 provides horizontal and vertical synchronization signals to the video signal interface 40, which outputs a video signal in a standard format such as NTSC, PAL, etc.

It is also possible to implement an equivalent system by illuminating the subject with more than one color at a time. For example, red light may be used during the first phase, and red and blue light may be used during the second phase. Then, the blue component may be computed by subtraction. Of course, other combinations of colors may be used as well.

By using this system, a monochromatic image sensor may be used in place of a full color image sensor. This is advantageous because monochromatic image sensors are significantly less expensive. In this configuration, to achieve a standard video frame rate of 30 frames per second, the frame rate at the image sensor must be tripled (i.e., to 90 frames per second). As a result, one red, one green and one blue image is captured by the image sensor in each $\frac{1}{30}$ second interval. These images are stored in the signal processor 39 and output at the standard frame rate.

Preferably, the signal processor 39 includes white balance circuitry that adjusts the proportions of the red, green, and blue images to produce a color-corrected image. Alternatively, the LED sequencer 36 can vary the brightness and/or duration of the red, blue, and green illumination to achieve color corrected images.

The combination of features described above allows the camera to be lighter, more portable, consume less power, and to produce a more authentic image than previous cameras.

While the present invention has been described above in terms of specific embodiments, it is to be understood that the invention is not limited to the disclosed embodiments. On the contrary, the present invention is intended to cover various modifications and equivalent structures included within the spirit and scope of the appended claims.

We claim:

1. A dental video camera comprising:
   a housing having a proximal end and a distal end;
   a window, located near the distal end of said housing, that receives light reflected from a subject;
   light directing means for directing the received light in a proximal direction;
   an image sensor, mounted on the proximal side of said light directing means, that receives the light directed by said light directing means; and
   a lamp mounted distally beyond the window, aimed to illuminate the subject, wherein said lamp comprises a plurality of different colored LEDs.

2. A dental video camera comprising:
   a housing having a proximal end and a distal end;
   a window, located near the distal end of said housing, for receiving light reflected from a subject;
   light directing means for directing the received light in a proximal direction;
   an image sensor, mounted on the proximal side of said light directing means, that receives the light directed by said light directing means; and a lamp mounted distally beyond the window, aimed to illuminate the subject, wherein said lamp comprises a phosphorescent material and an LED that illuminates the phosphorescent material, causing the phosphorescent material to emit visible light.

3. A dental video camera comprising:

a housing having a Proximal end and a distal end;

a window, located near the distal end of said housing, that receives light reflected from a subject, the window having a proximal edge, a distal edge, a right edge, and a left edge;

light directing means for directing the received light in a proximal direction;

an image sensor, mounted on the proximal side of said light directing means, that receives the light directed by said light directing means;

a plurality of lamps mounted distally beyond the window and aimed to illuminate the subject;

a plurality of lamps mounted adjacent to the right side of the window and aimed to illuminate the subject; and a plurality of lamps mounted adjacent to the left side of the window and aimed to illuminate the subject.

4. The dental video camera according to claim 3, wherein each of said lamps comprises an LED.

5. The dental video camera according to claim 3, wherein each of said lamps comprises a white LED.

6. The dental video camera according to claim 3, further comprising a a plurality of lamps mounted adjacent to the proximal side of the window and aimed to illuminate the subject.

7. The dental video camera according to claim 6, wherein each of said lamps comprises an LED.

8. The dental video camera according to claim 6, wherein each of said lamps comprises a white LED.

9. A dental video camera comprising:

housing having a window that receives light reflected from a subject;

an image sensor mounted in said housing;

light directing means for directing the received light towards said image sensor; and a white LED mounted in said housing, aimed to illuminate the subject, wherein said white LED comprises a phosphorescent material and an LED that illuminates the phosphorescent material, causing the phosphorescent material to emit visible light.

10. A dental video camera comprising:

a housing having a window that receives light reflected from a subject;

an image sensor mounted in said housing;

light directing means for directing the received light towards said image sensor; and a white LED mounted in said housing, aimed to illuminate the subject, wherein said white LED comprises a plurality of different colored LEDs.

11. A dental video camera comprising:

a housing having a proximal end and a distal end;

window located near the distal end of said housing that receives light reflected from a subject;

a lens;

an image sensor, mounted on the proximal side of said lens, that receives light received by the window and directed by said lens; and a white LED aimed to illuminate the subject; wherein said white LED comprises a phosphorescent material and an LED that illuminates the phosphorescent material, causing the phosphorescent material to emit visible light.

12. A dental video camera comprising:

a housing having a proximal end and a distal end;

a window located near the distal end of said housing that receives light reflected from a subject;

a lens;

an image sensor, mounted on the proximal side of said lens, that receives light received by the window and directed by said lens; and a white LED aimed to illuminate the subject, wherein said white LED comprises a plurality of different colored LEDs.

13. A method of using an image sensor to obtain an image of a dental subject, comprising the steps of:

illuminating the dental subject with light from a white LED;

receiving light reflected from the dental subject; and directing the received light towards the image sensor, wherein the white LED comprises a phosphorescent material and an LED that illuminates the phosphorescent material, causing the phosphorescent material to emit visible light.

14. A method of using an image sensor to obtain an image of a dental subject, comprising the steps of:

illuminating the dental subject with light from a white LED;

receiving light reflected from the dental subject; and directing the received light towards the image sensor, wherein the white LED comprises a plurality of different colored LEDs.

15. A dental video camera comprising:

first light source that produces a first color light;

a second light source that produces a second color light;

a third light source that produces a third color light;

a controller that controls illumination of said first, second, and third light sources according to a pattern;

an image sensor that receives light from said light sources that has been reflected by a subject and that generates output signals in accordance with the received light;

an image processor that generates a video signal based on the outputs of said image sensor, wherein said light sources are arranged about a light receiving window on three sides, including a distal side, of the light receiving window.

16. The dental video camera according to claim 15, wherein a light source of each color is included on each of the three sides of the light receiving window.

17. A dental video camera comprising:

a first light source that produces a first color light;

a second light source that produces a second color light;

a third light source that produces a third color light;

a controller that controls illumination of said first, second, and third light sources according to a pattern;

an image sensor that receives light from said light sources that has been reflected by a subject and that generates output signals in accordance with the received light;

an image processor that generates a video signal based on the outputs of said image sensor, wherein said light sources are arranged about a light receiving window on four sides of the light receiving window.

18. The dental video camera according to claim 17, wherein a light source of each color is included on each of the four sides of the light receiving window.

* * * * *